US007015486B1

(12) United States Patent
Sarbach et al.

(10) Patent No.: US 7,015,486 B1
(45) Date of Patent: Mar. 21, 2006

(54) FLUORESCENCE IMAGE ACQUISITION APPARATUS AND IMAGING SYSTEM COMPRISING SUCH AN APPARATUS

(75) Inventors: Christian Sarbach, Versailles (FR); Pascal Delvordre, Massy (FR); Pierre-Michel Baron, Courbevoie (FR)

(73) Assignee: AR21 SA - Analyses, Recherches et Innovation Instrumentale, (FR)

(*) Notice: Subject to any disclaimer, the term of this patent is extended or adjusted under 35 U.S.C. 154(b) by 0 days.

(21) Appl. No.: 09/856,597

(22) PCT Filed: Nov. 19, 1999

(86) PCT No.: PCT/FR99/02847

§ 371 (c)(1),
(2), (4) Date: Jul. 23, 2001

(87) PCT Pub. No.: WO00/31962

PCT Pub. Date: Jun. 2, 2000

(30) Foreign Application Priority Data

Nov. 24, 1998 (FR) .................................. 98 14762

(51) Int. Cl.
*G01N 21/64* (2006.01)

(52) U.S. Cl. ............................. 250/461.1; 250/458.1

(58) Field of Classification Search ............. 250/461.1, 250/458.1
See application file for complete search history.

(56) References Cited

U.S. PATENT DOCUMENTS

| 4,747,686 A | * | 5/1988 | Sato ........................... 356/72 |
| 4,884,200 A | * | 11/1989 | Kimura et al. .............. 382/129 |
| 5,149,972 A | * | 9/1992 | Fay et al. ................. 250/461.1 |
| 6,092,924 A | * | 7/2000 | Scalese et al. ................ 374/14 |

FOREIGN PATENT DOCUMENTS

| DE | 3528216 | 2/1986 |
| DE | 3544202 | 6/1986 |
| DE | 3513519 | 10/1986 |
| EP | 0747753 | 12/1996 |
| JP | 63052574 | 3/1988 |
| JP | 05316279 | 11/1993 |
| JP | 08050338 | 2/1996 |
| JP | 09098302 | 4/1997 |
| JP | 10150553 | 6/1998 |

* cited by examiner

*Primary Examiner*—Otilia Gabor
*Assistant Examiner*—Christine Sung
(74) *Attorney, Agent, or Firm*—Michael Best & Friedrich LLP

(57) ABSTRACT

The invention concerns an image acquisition apparatus comprising a UV radiation source (29) capable of making fluorescent supports (1) whereof the images are to be acquired, a window (21) transparent to UV and visible light, typically rectangular, for receiving an image support to be acquired, a linear sensor (31) whereof the length is preferably substantially equal to the width of the window receiving a support and means (23) driving the sensor and, preferably the UV radiation source parallel to one of the edges of the window (21) receiving an image support. The invention is mainly applicable to image acquisition for revealing a chemical or physical phenomenon. The invention is mainly applicable to planar chromatography or layer chromatography.

9 Claims, 2 Drawing Sheets

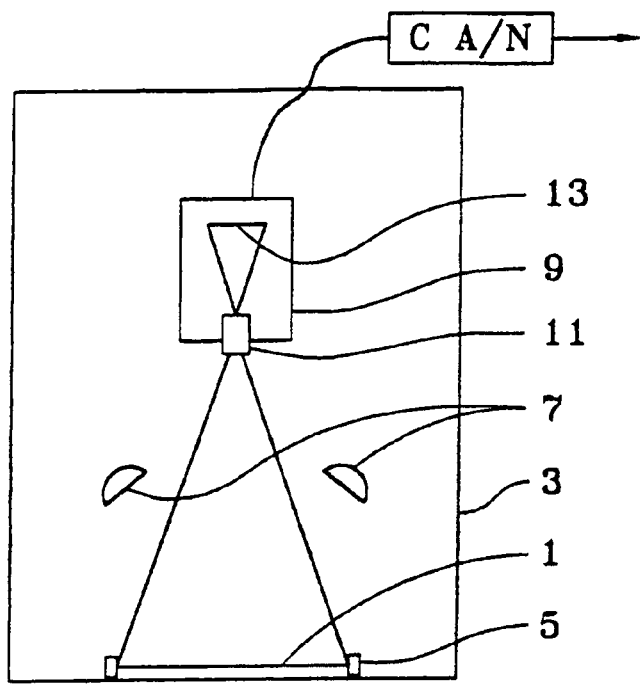
FIG. 1
PRIOR ART
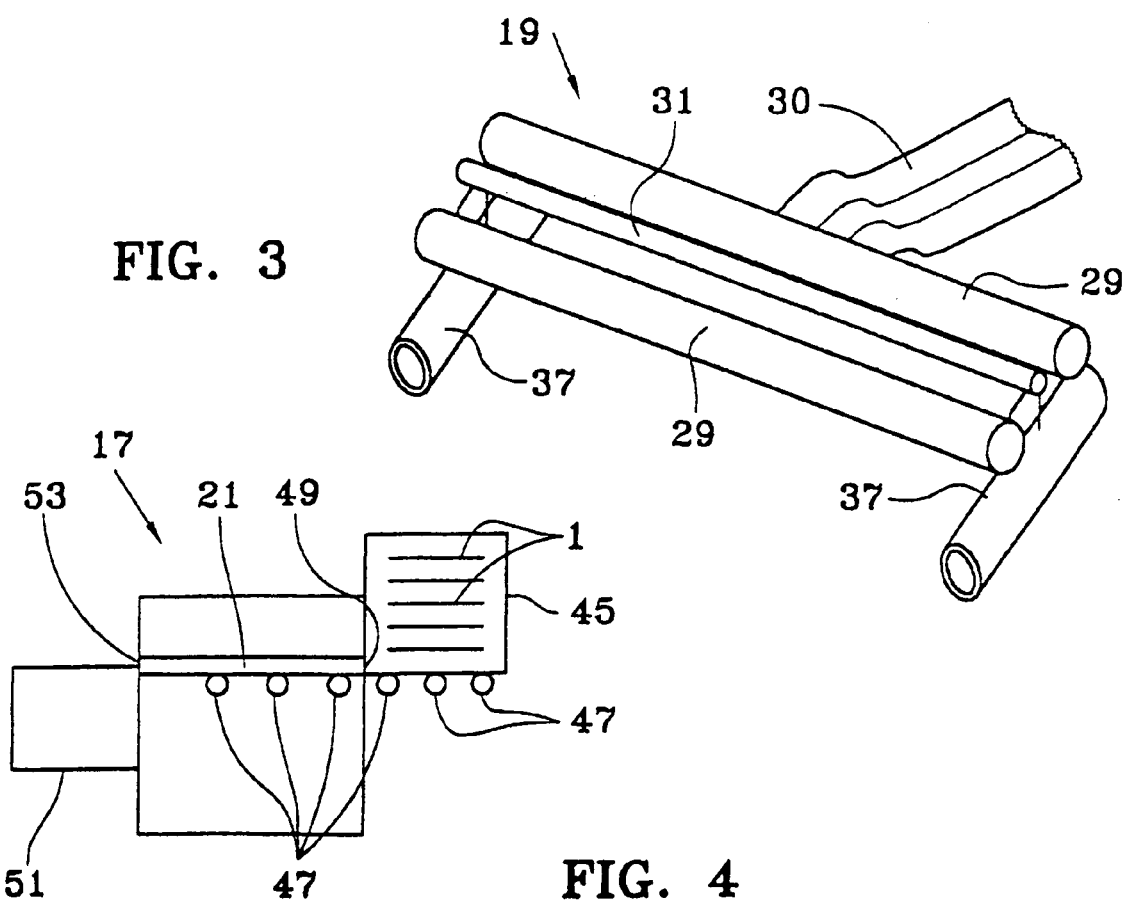
FIG. 3
FIG. 4

FLUORESCENCE IMAGE ACQUISITION APPARATUS AND IMAGING SYSTEM COMPRISING SUCH AN APPARATUS

The present invention relates mainly to a fluorescence image acquisition apparatus and to an imaging system comprising such an apparatus.

It is known to illuminate planar chromatography or thin-layer chromatography supports with ultraviolet (UV) radiation and to acquire, using a video camera, images of these supports which are rendered fluorescent. This technique has many drawbacks.

The distance between the chromatography plate and the sensor is determined by the optical characteristics (focusing, focal length, etc.) of the objective used. The apparatuses of the known type are bulky.

The low resolution and limited surface area of the sensors of the CCD (charge-coupled device) type, in particular the sensor having a 0.85 mm (⅓ of an inch) diagonal limits the definition of the image to typically 732×580 picture elements or pixels.

The apparatuses of the known type have a high manufacturing cost, especially because they use a large darkroom for illumination and image acquisition and because the video cameras used correspond to non-standardized professional equipment.

In addition, the apparatuses of the known type are not easy to handle; after having cut the UV source the darkroom must be opened in order to remove the treated chromatography plate, in order to replace it with the next chromatography plate, and the darkroom must be closed again before being able to turn the UV source on for the next acquisition.

It is consequently an object of the present invention to provide an apparatus for the acquisition, by fluorescence, of high-definition images of a plane or substantially plane support.

It is also an object of the present invention to provide such an apparatus which is very reliable.

It is also an object of the present invention to provide such an apparatus which does not present a hazard for an operator.

It is also an object of the present invention to provide such an apparatus which is compact.

It is also an object of the present invention to provide a rapid image acquisition apparatus.

It is also an object of the present invention to provide an image acquisition apparatus which is easy to use.

It is also an object of the present invention to provide an automatic image acquisition system capable of processing a plurality of chromatography supports autonomously.

It is also an object of the present invention to provide such an apparatus or such a system at a moderate manufacturing cost.

These objectives are achieved by an image acquisition apparatus according to the present invention, which comprises a UV radiation source capable of making the supports, the image of which it is desired to acquire, fluorescent, a window transparent to UV and to visible light, typically rectangular, for housing a support for the image to be acquired, a linear sensor, the length of which is preferably approximately equal to the width of the window for housing a support, and means for driving the sensor and, preferably, the UV radiation source parallel to one of the edges of the window for housing an image support.

The subject of the invention is mainly an apparatus for the acquisition of fluorescent images of a plane object, comprising means for housing the plane object whose image it is desired to acquire, a UV radiation source inducing the photoluminescence of said object and a sensor sensitive to the fluorescent radiation, characterized in that it includes a carriage which supports a linear sensor provided with a plurality of aligned photosites and means for driving the carriage which supports the linear sensor with respect to the region of the object whose image it is desired to acquire and control means for controlling the illumination with UV radiation and for moving the carriage with respect to the object, with the acquisition of a succession of image lines corresponding to at least one region of the plane object whose image it is desired to acquire.

The subject of the invention is also an image acquisition apparatus, characterized in that said apparatus is a flat digitizer with means for holding the object stationary and for moving the carriage.

The subject of the invention is also an apparatus characterized in that the carriage furthermore includes at least one UV radiation source.

The invention also has [sic] an apparatus characterized in that the UV radiation source is a linear source placed parallel to the linear sensor.

The subject of the invention is also an apparatus, characterized in that it includes a window without a pane and corresponding to the acquisition region scanned by the carriage.

The subject of the invention is also an apparatus, characterized in that it includes a window corresponding to the acquisition region of the object, provided with a pane made of a material transparent to the fluorescent visible radiation and to the radiation inducing the photoluminescence.

The subject of the invention is also an apparatus, characterized in that it includes multiple UV radiation sources corresponding to several UV radiation wavelengths.

The subject of the invention is also an apparatus, characterized in that it includes a cover provided with means for automatically stopping the emission of UV radiation if the cover is not properly closed.

The subject of the invention is also an apparatus, characterized in that it includes a charger ensuring that the image acquisition window is automatically supplied with a rigid chromatography plate.

The subject of the invention is also a system for the processing of fluorescent planar-chromatography images, characterized in that it includes an apparatus according to the invention combined with a computer provided with image processing software.

The invention will be more clearly understood by means of the description below and the appended figures given as non-limiting examples, in which:

FIG. 1 is a schematic cross-sectional view of an image acquisition device of a known type;

FIG. 3 is a perspective view of an embodiment of a carriage used in the apparatus of FIG. 2;

FIG. 4 is a schematic cross-sectional view in a vertical plane of an embodiment of an apparatus according to the present invention provided with an automatic charger.

In FIGS. 1 to 4, the same reference numbers have been used to denote the same components.

Figure 2:
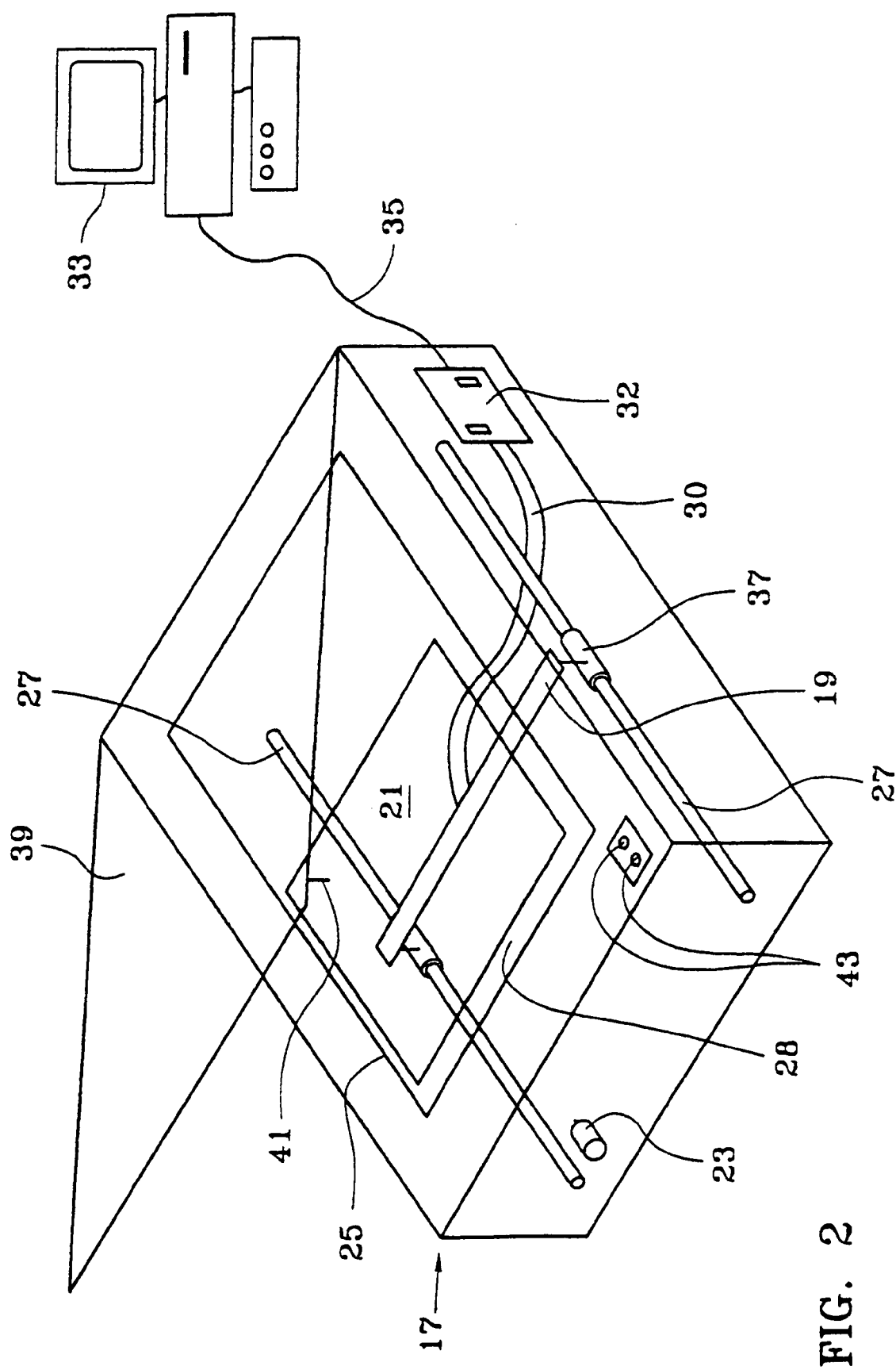
FIG. 2 is a schematic perspective view of the preferred embodiment of an apparatus according to the present invention.

FIG. 1 shows an embodiment of an apparatus of known type for the acquisition of fluorescent images of a chromatography plate 1, comprising an enclosure 3 impermeable to visible light and to UV radiation, a support 5 for the chromatography plate 1, an illumination device 7, comprising one or more UV radiation sources, which is directed toward the support 5 and a video camera 9. The camera 9 typically has a fixed-focus objective 11 or a zoom, ensuring the formation of an image on a sensor 13 of the charge-coupled type. The image obtained by the camera 9 is processed by digital processing means, typically a microcomputer. The output of the camera 9 is connected to an analog-to-digital converter 15 which may be incorporated into the acquisition apparatus, may form an independent electronic unit or may be incorporated into an acquisition card of a computer.

The dimensions of the enclosure 3 forming the darkroom are mainly determined by the distance separating the objective 11 from the focal plane corresponding to the support 1, determined by the characteristics of the camera 9 and especially by the focal length of the objective, by the focusing carried out and especially by the distance between the objective and the plane of the video sensor 13. Apart from the abovementioned drawbacks relating to the bulk, the low definition of the images provided by the camera 9 and the handling problem, the apparatus in FIG. 1 must be provided with a powerful UV source 7 capable of uniformly illuminating, simultaneously, the entire surface of the plate 1.

The apparatus according to the present invention can be easily produced from available standard components or, advantageously, as illustrated in FIG. 2, can be made by modifying a digitizer (or scanner) intended for office automation and/or graphical artwork. The apparatus 17 according to the present invention includes a carriage 19 capable, upon command, of moving past a window 21 for housing an image support, such as a rigid chromatography plate or a flexible support. The carriage 19 is driven by driving means 23, typically an electric stepper motor driving a cogged endless belt. The carriage 19 is guided by one or preferably two guide rails 27 placed parallel to the longitudinal edge 25 of the window 21. The rail 27 is made from folded sheet or, advantageously, consists of a metal section, for example a cylindrical section. The carriage 19 supports, on the one hand, one or more UV radiation sources 29 and, on the other hand, a linear video sensor 31, typically a linear array of charge-coupled devices extending over the entire width of the window 21. Likewise, the sources 29 advantageously extend parallel to the sensor 31 over the entire width of the window 21. As a variant, the UV radiation sources 29 are stationary. The sources 29 and the video sensor 31 may be associated with optical components, such as lenses, especially cylindrical lenses, or return mirrors. It is essential that the window 21 allow transmission of the radiation for illuminating the support, especially a chromatography plate, coming from the sources 29 and propagation of this light coming, by reflection or fluorescence, from the support 1 onto the sensor 31. Thus, the window 21 may have no pane, the support being formed by the longitudinal rim 25 and/or a transverse rim 28 and/or by a frame placed on these rims in the case of a chromatography plate having dimensions smaller than those of the window 21. On the other hand, the window 21 may be provided with a window transparent to the wavelengths used, especially to UV radiation and to visible light. It is possible, for example, to use a pane made of quartz or of plastic transparent to visible and UV radiation. The carriage 19 is connected via a cable 30, for example a ribbon cable, to an electronic card 32 for controlling the components of the digitizer, for shaping the signals, especially sampling, for example over 24, 30 or advantageously 36 bits (8, 10 or 12 bits per primary color), and for communicating with an external machine 33, for example with a microcomputer provided with a parallel or SCSI interface card, the interface card being connected to the scanner via a cable 35. Advantageously, an image is transmitted to the computer without reducing the dynamic range of the images coded, for example, over 24, 30 or 36 bits. The carriage 19 furthermore includes means for switching the light sources 29 and the video sensor 31, as well as means 37 for mechanical coupling to the rails 27, for example bushes in the case of cylindrical rails and means for coupling to the drive belt. The cover 39, opaque to visible light and to UV radiation protects the video sensor 31 from any spurious light getting in, and simultaneously protects the operator against irradiation by the UV radiation. Advantageously, the cover 39 is provided with means 41 for turning the sources 29 off should the cover be opened. For example, the cover is provided with a conducting element 41 which ensures, when the cover is closed, that there is electrical continuity between terminals 43 placed in the body of the digitizer 17 and connected in series with the electrical supply source 29. Thus, accidental opening of the cover 39 instantly stops the emission of UV light toward the operator and thus prevents him from being irradiated by radiation which could prove to be hazardous to his health.

The carriage 19 includes, for example, a source 29, capable of emitting UV radiation at 254 nm, a source 29 capable of emitting UV radiation at a wavelength of 365 nm, or a UV source which can be tuned to these two frequencies, together with a source of visible light. Of course, the use of radiation having other wavelengths does not lie outside the scope of the present invention. The video sensor 31 has, for example, 2587 photosites distributed over a length of 219 mm corresponding to a resolution of 300 dots per inch or 5174 photosites distributed over 219 mm, corresponding to a resolution of 600 dots per inch, or 10 348 photosites distributed over 219 nm, corresponding to a resolution of 1200 dots per inch.

The carriage 19, the guiding means 27 and 37, and/or the drive means, such as the motor 23 or the cogged belt, may advantageously be strengthened so as to withstand the weight of the additional light source without any loss of precision in the movement of the carriage, typically between 76.2 dots per mm (300 dots per inch), 152 dots per mm (corresponding to 154.4 dots per inch), 304.8 dots per mm (corresponding to 1200 dots per inch) or 609.6 dots per mm (corresponding to 2400 dots per inch).

In the preferred embodiment, the digitizer 17 is a flat digitizer. However, the use of other digitizer types such as, for example, running digitizers or digitizers for slides, in which one or more sources 29 would be placed on one side of the video sensor, is not outside the scope of the present invention. Likewise, it is possible to adapt a flat scanner with a slide holder, such as the scanners sold under the name DUOSCAN by the company AGFA in order for chromatography plates to be digitized according to the present invention. In this case too, the sources 29 are placed on the same side as the video sensor. The latter type of scanner has the advantage of not requiring a pane made of UV transparent material, while still ensuring that the mechanism of the digitizer is protected from dust.

FIG. 4 shows an alternative embodiment of an apparatus according to the present invention, provided with an automatic charger for charging with rigid chromatography plates 1. The apparatus 17 is provided, on the one hand, with a magazine 45 for housing a stack of plates resting on a number of rollers 47, at least one of which is motorized. The rollers 47 are placed opposite a slot 49 for housing the support 1 in the apparatus 17. The window 21 is also provided with rollers 47 for ejecting a digitized plate into a magazine 51 located, for example, beneath a slot 53 for ejecting the processed chromatography plates 1 placed opposite the slot 49.

The picture-taking apparatus 17 according to the present invention operates in the following manner:

A conventional planar chromatography plate is placed in front of the window 21, especially on the rims 25 and 28, or in the magazine 45. In the latter case, a logic command issued by the computer 33 makes the plate move past the window 21. The plate may include, in addition to a chromatography support of known type, identification means, such as a bar code or, advantageously, characters identifiable by optical character recognition. The characters are advantageously printed in an easily identifiable font, such as ROC B. Thus, the high definition of the image acquired by the apparatus 17 according to the present invention can be used to achieve one-to-one correspondence between acquired images and controls corresponding to specimens processed by chromatography.

The cover 39 is closed again. The apparatus 17 receives a command from the computer 33, a factory-programmed command or a command entered via a keyboard (not shown) of the apparatus. This command corresponds to turning a light source 29 on and to scanning the surface of the plate 1 with successive acquisition of all the lines of the image which is simultaneously transmitted to the computer 33. The scanning can then be carried out at a different frequency (UV or visible) so as, in the latter case, to detect colored molecules directly or after the action of a more or less specific developer. The fluorescence allows the detection of directly fluorescent molecules or the reading of fluorescence inhibition of a plate containing a fluorescence indicator. The images acquired are advantageously stored in a conventional bulk memory, for example a hard disk of the computer 33 which carries out the processing according to the strict rules of "good laboratory practice", so as to obtain qualitative and quantitative results of spots likely to be present on the plate 1. A software package sold under the name BORWIN by the company JMBS may, for example, be used. This software package may be supplemented with a software package for optical character recognition or for reading bar codes. The identified characters or the decoded code is [sic] associated, in the form of references, comments or filenames, with the processed images.

The apparatus according to the present invention makes it possible to improve the precision of the processing insofar as it provides the image processing software with a high-definition image comprising, for example, 4724 dots by 4724 dots (for a digitizer resolution of 600 dots per inch) or a definition of 9448 dots by 9448 dots for a definition of 1200 dots per inch, or for plates having sides of 20 cm.

The present invention is not limited to chromatography, but applies to all types of acquisition of high-definition fluorescent images. Likewise, it may replace or complement the video sensor with a sensor which is sensitive to UV or other radiation.

The present invention applies mainly to image acquisition corresponding to the revelation of a chemical or physical phenomenon.

The present invention applies mainly to planar chromatography or thin-layer chromatography.

The invention claimed is:

1. Apparatus for the acquisition of fluorescent images of a plane object, comprising
   means for housing the plane object whose image it is desired to acquire,
   a UV radiation source inducing photoluminescence of said object and
   a sensor sensitive to fluorescent radiation,
   characterized in that it includes a carriage which supports a linear sensor provided with a plurality of aligned photosites,
   at least one UV radiation source and means for driving the carriage which supports the linear sensor with respect to a region of the object whose image it is desired to acquire and
   control means for controlling illumination with UV radiation and for moving the carriage with respect to the object,
   with the acquisition of a succession of image lines corresponding to at least one region of the plane object whose image it is desired to acquire,
   characterized in that it includes a cover provided with means for automatically stopping the emission of UV radiation if the cover is not properly closed.

2. Apparatus according to claim 1, characterized in that said apparatus is a flat digitizer with means for holding the object stationary and for moving the carriage.

3. Apparatus according to claim 1, characterized in that the UV radiation source is a linear source placed parallel to the linear sensor.

4. Apparatus according to claim 1, characterized in that it includes a window without a pane and corresponding to an acquisition region scanned by the carriage.

5. Apparatus according to claim 1, characterized in that it includes a window corresponding to an acquisition region of the object, provided with a pane made of a material transparent to fluorescent visible radiation and to radiation inducing photoluminescence.

6. Apparatus according to claim 1, characterized in that it includes multiple UV radiation sources corresponding to several UV radiation wavelengths.

7. Apparatus according to claim 1, characterized in that it includes a charger ensuring that an image acquisition window is automatically supplied with a rigid chromatography plate.

8. Apparatus for the acquisition of fluorescent images of a plane object, comprising
   means for housing the plane object whose image it is desired to acquire,
   a UV radiation source inducing photoluminescence of said object and
   a sensor sensitive to fluorescent radiation,
   characterized in that it includes a carriage which supports a linear sensor provided with a plurality of aligned photosites,
   with at least one UV radiation source for emitting radiation at two wavelengths in order to carry out a chromatographic analysis for detection of directly fluorescent chemical substances and detection by a fluorescence inhibition method,
   at least one UV radiation source and means for driving the carriage which supports the linear sensor with respect to a region of the object whose image it is desired to acquire and
   control means for controlling illumination with UV radiation and for moving the carriage with respect to the object,
   with the acquisition of a succession of image lines corresponding to at least one region of the plane object whose image it is desired to acquire, characterized in that it includes a cover provided with means for automatically stopping the emission of UV radiation if the cover is not properly closed.

9. System for the processing of fluorescent planar-chromatography images, characterized in that it includes an apparatus comprising means for housing the plane object whose image it is desired to acquire, a UV radiation source inducing photoluminescence of said object and a sensor sensitive to fluorescent radiation, characterized in that it includes a carriage which supports a linear sensor provided with a plurality of aligned photosites, at least one UV radiation source and means for driving the carriage which supports the linear sensor with respect to a region of the object whose image it is desired to acquire and control means for controlling illumination with UV radiation and for moving the carriage with respect to the object, with the acquisition of a succession of image lines corresponding to at least one region of the plane object whose image it is desired to acquire, characterized in that it includes a cover provided with means for automatically stopping the emission of UV radiation if the cover is not properly closed, combined with a computer provided with image processing software.

* * * * *